(12) United States Patent
Sonnenberg et al.

(10) Patent No.: US 8,926,718 B2
(45) Date of Patent: Jan. 6, 2015

(54) THERMOCHEMICALLY PRODUCED ETHANOL COMPOSITIONS

(71) Applicant: Celanese International Corporation, Irving, TX (US)

(72) Inventors: Tatiana H. Sonnenberg, Houston, TX (US); R. Jay Warner, Houston, TX (US); Heiko Weiner, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 81 days.

(21) Appl. No.: 13/835,157

(22) Filed: Mar. 15, 2013

(65) Prior Publication Data

US 2014/0275637 A1    Sep. 18, 2014

(51) Int. Cl.
*C10L 1/18* (2006.01)
*C07C 29/147* (2006.01)
*C07C 31/08* (2006.01)

(52) U.S. Cl.
CPC ............ *C07C 29/147* (2013.01); *C07C 31/08* (2013.01)
USPC .......................................................... 44/452

(58) Field of Classification Search
CPC ............................ C07C 29/147; C07C 31/08
USPC .......................................................... 44/452
See application file for complete search history.

(56) References Cited

U.S. PATENT DOCUMENTS

| | | |
|---|---|---|
| 1,469,447 A | 10/1923 | Schneible |
| 2,549,416 A | 4/1951 | Brooks |
| 2,591,671 A | 4/1952 | Catterall |
| 2,591,672 A | 4/1952 | Catterall |
| 2,607,719 A | 8/1952 | Eliot et al. |
| 2,702,783 A | 2/1955 | Harrison et al. |
| 2,715,604 A | 8/1955 | Weaver, Jr. |
| 2,744,939 A | 5/1956 | Kennel |
| 2,801,209 A | 7/1957 | Muller et al. |
| 3,404,186 A | 10/1968 | Bailey et al. |
| 3,408,267 A | 10/1968 | Miller et al. |
| 3,445,345 A | 5/1969 | Katzen et al. |
| 3,990,952 A | 11/1976 | Katzen et al. |
| 4,306,942 A | 12/1981 | Brush et al. |
| 4,319,058 A | 3/1982 | Kulprathipanja et al. |
| 4,395,576 A | 7/1983 | Kwantes et al. |
| 4,422,903 A | 12/1983 | Messick et al. |
| 4,426,541 A | 1/1984 | King |
| 4,448,644 A | 5/1984 | Foster et al. |
| 4,454,358 A | 6/1984 | Kummer et al. |
| 4,492,808 A | 1/1985 | Hagen et al. |
| 4,517,391 A | 5/1985 | Schuster et al. |
| 4,520,213 A | 5/1985 | Victor |
| 4,541,897 A | 9/1985 | Sommer et al. |
| 4,600,571 A | 7/1986 | McCarroll et al. |
| 4,678,543 A | 7/1987 | Houben et al. |
| 4,760,171 A | 7/1988 | Isogai et al. |
| 4,761,505 A | 8/1988 | Diana et al. |
| 4,774,365 A | 9/1988 | Chen et al. |
| 4,842,693 A | 6/1989 | Wheldon |
| 4,880,937 A | 11/1989 | Matsushita et al. |
| 4,943,354 A | 7/1990 | Osterburg et al. |
| 5,035,776 A | 7/1991 | Knapp |
| 5,070,016 A | 12/1991 | Hallberg et al. |
| 5,081,321 A | 1/1992 | Fukuhara et al. |
| 5,124,004 A | 6/1992 | Grethlein et al. |
| 5,185,481 A | 2/1993 | Muto et al. |
| 5,215,902 A | 6/1993 | Tedder |
| 5,250,271 A | 10/1993 | Horizoe et al. |
| 5,284,983 A | 2/1994 | Muto et al. |
| 5,415,741 A | 5/1995 | Berg |
| 5,445,716 A | 8/1995 | Berg |
| 5,449,440 A | 9/1995 | Rescalli et al. |
| 5,488,185 A | 1/1996 | Ramachandran et al. |
| 5,720,784 A | 2/1998 | Killick et al. |
| 5,800,681 A | 9/1998 | Berg |
| 5,858,031 A | 1/1999 | Perlman |
| 6,462,231 B1 | 10/2002 | Yanagawa et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,632,330 B1 | 10/2003 | Colley et al. |
| 6,809,217 B1 | 10/2004 | Colley et al. |
| 7,074,603 B2 | 7/2006 | Verser et al. |
| 7,361,794 B2 | 4/2008 | Grosso |
| 7,399,892 B2 | 7/2008 | Rix et al. |
| 7,425,657 B1 | 9/2008 | Elliott et al. |
| 7,507,562 B2 | 3/2009 | Verser et al. |
| 7,553,397 B1 | 6/2009 | Colley et al. |
| 7,572,353 B1 | 8/2009 | Vander et al. |

(Continued)

FOREIGN PATENT DOCUMENTS

| | | |
|---|---|---|
| CN | 1230458 | 10/1999 |
| CN | 201768393 | 3/2011 |
| CN | 102091429 | 6/2011 |
| CN | 101525272 | 5/2012 |
| DE | 2723611 | 11/1973 |
| EP | 0104197 | 4/1984 |
| EP | 0137749 | 4/1985 |
| EP | 2060553 | 5/2009 |
| JP | 4193304 | 7/1992 |
| JP | 2009-263356 | 11/2009 |

(Continued)

OTHER PUBLICATIONS

International Fuel Quality Center Hart Downstream Energy Services: "Setting a quality standard for fuel ethanol—DEH ethanol standard 18/2004 report", Jan. 1, 2004, pp. 1-56.

(Continued)

*Primary Examiner* — Elvis O Price (57) ABSTRACT

In one embodiment, the present invention is to an ethanol composition comprising at least 92 wt. % ethanol and from 20 wppm to 94 wppm isopropanol. The composition may be free of methanol and acetaldehyde.

20 Claims, 3 Drawing Sheets

(56) References Cited

U.S. PATENT DOCUMENTS

| | | |
|---|---|---|
| 7,594,981 B2 | 9/2009 | Ikeda |
| 7,732,173 B2 | 6/2010 | Mairal et al. |
| 7,744,727 B2 | 6/2010 | Blum et al. |
| 7,790,938 B2 | 9/2010 | Kawasaki et al. |
| 7,842,844 B2 | 11/2010 | Atkins |
| 7,888,082 B2 | 2/2011 | Verser et al. |
| 7,947,746 B2 | 5/2011 | Daniel et al. |
| 7,964,379 B2 | 6/2011 | Verser et al. |
| 8,002,953 B2 | 8/2011 | Lee et al. |
| 8,053,610 B2 | 11/2011 | Kikuchi et al. |
| 8,071,389 B2 | 12/2011 | Weck et al. |
| 8,088,832 B2 | 1/2012 | Melnichuk et al. |
| 8,128,826 B2 | 3/2012 | Plante et al. |
| 8,129,436 B2 | 3/2012 | Tirtowidjojo et al. |
| 8,198,057 B2 | 6/2012 | Padgett |
| 8,232,440 B2 | 7/2012 | Holtzapple et al. |
| 8,288,596 B2 | 10/2012 | Garton et al. |
| 8,299,132 B2 | 10/2012 | Gracey et al. |
| 8,299,133 B2 | 10/2012 | Gracey et al. |
| 8,460,405 B2 | 6/2013 | Horton et al. |
| 2003/0153059 A1 | 8/2003 | Pilkington et al. |
| 2004/0063184 A1 | 4/2004 | Grichko |
| 2005/0214408 A1 | 9/2005 | Pilkington et al. |
| 2007/0138083 A1 | 6/2007 | Aizawa |
| 2007/0144886 A1 | 6/2007 | Sylvester et al. |
| 2008/0135396 A1 | 6/2008 | Blum |
| 2009/0166172 A1 | 7/2009 | Casey |
| 2010/0270139 A1 | 10/2010 | Halvorsen et al. |
| 2011/0004034 A1 | 1/2011 | Daniel et al. |
| 2011/0046421 A1 | 2/2011 | Daniel et al. |
| 2011/0224462 A1 | 9/2011 | Ditzel et al. |
| 2012/0010442 A1 | 1/2012 | Sarager et al. |
| 2012/0041075 A1 | 2/2012 | Johnston et al. |
| 2012/0277488 A1 | 11/2012 | Horton et al. |
| 2013/0172631 A1 | 7/2013 | Warner et al. |
| 2014/0094629 A1 | 4/2014 | Sarager et al. |

FOREIGN PATENT DOCUMENTS

| | | |
|---|---|---|
| JP | 2010-159212 | 7/2010 |
| WO | WO 2007/004789 | 1/2007 |
| WO | WO 2008/135192 | 11/2008 |
| WO | WO 2009/009320 | 1/2009 |
| WO | WO 2009/009322 | 1/2009 |

OTHER PUBLICATIONS

Ivan Hodac, et al., "Ethanol Guidelines", Mar. 1, 2009, pp. 1-12.
International Search Report and Written Opinion for PCT/US2014/028034 mailed Aug. 4, 2014.

THERMOCHEMICALLY PRODUCED ETHANOL COMPOSITIONS

FIELD OF THE INVENTION

The present invention relates generally to thermochemical processes for producing ethanol compositions, and to processes for purifying the ethanol compositions obtained from these processes. The thermochemical process controls secondary alcohols in the ethanol composition, and avoids having to separate the secondary alcohols during the purification.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption. In addition, fermentation of starchy or cellulose materials competes with food sources and places restraints on the amount of ethanol that can be produced for industrial use.

Conventional ethanol compositions are formed as a result of the above-identified processes that contain impurities which must be removed.

For example, U.S. Pat. No. 5,488,185 utilizes a petrochemical feed stock and relates to an ethene stream which contains ethane as an impurity or a propene stream which contains propane as an impurity that is hydrated with water vapor in the presence of a hydration catalyst to produce ethanol or isopropanol, respectively. After removal of the alcohol the gaseous product stream is subjected to adsorption, thereby producing an ethene-enriched stream or a propene-enriched stream. The ethene-enriched stream or the propene-enriched stream is recycled to the hydration reactor.

U.S. Pat. Nos. 5,185,481 and 5,284,983 relate to conventional fermentation methods for producing ethanol. The produced ethanol compositions comprise impurities such as methanol, acetaldehyde, n-propanol, n-butanol, ethyl acetate, 3-methylbutanol, diethyl ether, acetone, secondary butanol, and crotonaldehyde. These references also disclose separation methods for treating the crude ethanol aqueous solution with an extracting solvent comprising carbon dioxide in a liquid state or carbon dioxide in a super-critical state.

U.S. Pat. Nos. 5,445,716; 5,800,681; and 5,415,741 relate to separation methods for mixtures of ethanol and isopropanol. Ethanol is difficult to separate from isopropanol by conventional distillation or rectification because of the proximity of their boiling points. Ethanol can be readily separated from isopropanol by extractive distillation. Effective extractive agents are dipentene, anisole, and ethyl benzene. The mixtures in these references, comprise a significant amount of isopropanol, e.g., at least 21.5 wt. % isopropanol.

Also, U.S. Pat. No. 5,858,031 relates to a method for enhancing the visibility of a flame produced during free-burning of an aqueous alcohol-based fuel composition in air. The fuel includes between approximately 10% and 30% by volume of water, and between approximately 70% and 90% by volume of a mixture of alcohols including ethanol and isopropanol, the ethanol constituting between approximately 24% and 83% by volume of the fuel composition. The method includes providing an amount of isopropanol ranging between approximately 7% and 60% by volume of the fuel composition, in which the volume ratio of isopropanol to ethanol in the fuel does not exceed 2:1.

U.S. Pat. No. 5,081,321 relates to isopropanol preparation through catalytic hydrogenation of acetone. The reaction may preferably be effected at a temperature of from room temperature to 200° C., although an industrial reaction rate is achieved at a reaction temperature of from 35 to 150° C. Too high of a reaction temperature induces excess hydrogenation decomposition of acetone, resulting in reduced yields of isopropanol.

Although conventional processes may produce and/or purify ethanol compositions, these processes rely on petrochemical feed stocks or fermentation techniques to yield the ethanol compositions. Further, in the resultant ethanol compositions that do comprise isopropanol, the isopropanol is present in large amounts.

Therefore, the need exists for an ethanol production process that reduces and/or controls isopropanol content.

SUMMARY OF THE INVENTION

In a first embodiment, the present invention is directed to a thermochemically formed ethanol composition comprising: at least 92 wt. % ethanol; and from 20 to 94 wppm isopropanol; wherein the ethanol composition is free of methanol and acetaldehyde. The ethanol composition may be formed by hydrogenating acetic acid and/or an ester thereof. In some embodiments, the ethanol composition may comprises from 20 to 80 wppm isopropanol. The ethanol composition may comprise from 3 to 8 wt. % water. The ethanol composition may comprise less than 0.005 wt. % acetone. The ethanol composition may comprise less than 1 wt. % acetic acid. The ethanol composition may comprise less than 2 wt. % ethyl acetate. The ethanol composition may comprise less than 0.5 wt. % butanol, isobutanol, isoamyl alcohol and $C_4$-$C_{20}$ alcohols.

In a second embodiment, the present invention is directed to a process for preparing an ethanol composition comprising: hydrogenating an alkanoic acid and/or an ester thereof to form a crude ethanol product; and recovering a final ethanol product; wherein the final ethanol product comprises at least 92 wt. % ethanol and from 20 to 94 wppm isopropanol, and further wherein the final ethanol product is free of methanol and acetaldehyde. The alkanoic acid may be acetic acid. The hydrogenating may be performed at a temperature from 250° C. to 285° C. The hydrogenating may be performed at a temperature from 250° C. to 275° C. The hydrogenating may be in the presence of a catalyst on a support, wherein the catalyst comprises at least one active metal selected from the group consisting of cobalt, nickel, rhodium, palladium, osmium, iridium, platinum, titanium, zinc, chromium, rhenium, molybdenum, ruthenium, tin, vanadium, lanthanum, cerium, manganese, gold, and combinations thereof. The support may comprise a support modifier selected from the group consisting of $TiO_2$, $ZrO_2$, $Ta_2O_5$, $Al_2O_3$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In a third embodiment, the present invention is directed to a process for controlling isopropanol content in an ethanol production process comprising: hydrogenating acetic acid and/or an ester thereof in a reactor in the presence of a catalyst to form a crude ethanol product; separating the crude ethanol product in at least one distillation column to recover an intermediate ethanol product; measuring the content of isopropanol in the intermediate ethanol product, adjusting the temperature of the reactor, and recovering a finished ethanol product comprising at least 92 wt. % ethanol and from 20 to 94 wppm isopropanol, and wherein the finished ethanol product is free of methanol and acetaldehyde. The temperature in the reactor may be between 250° C. and 280° C. The adjusting the temperature of the reactor may comprise reducing the temperature of the reactor by at least 2° C. when the isopropanol content in the intermediate ethanol product is greater than 100 wppm. The adjusting the temperature of the reactor may comprise increasing the temperature of the reactor by at least 2° C. when the isopropanol content in the intermediate ethanol product is less than 20 wppm. The finished ethanol product may be free of acetone. The crude ethanol product may be free of isopropanol.

In a fourth embodiment, the present invention is directed to a thermochemically formed ethanol composition comprising at least 92 wt. % ethanol, e.g., from 93 to 96 wt. % ethanol, from 3 to 8 wt. % water, and from 20 to 94 wppm isopropanol, e.g., from 20 to 80 wppm isopropanol, wherein the ethanol composition is free of methanol and acetaldehyde.

In a fifth embodiment, the present invention is directed to a thermochemically formed ethanol composition comprising at least 92 wt. % ethanol, e.g., from 93 to 96 wt. % ethanol, less than 0.005 wt. % acetone, e.g., from 0.001 to 0.005 acetone, and from 20 to 94 wppm isopropanol, e.g., from 20 to 80 wppm isopropanol, wherein the ethanol composition is free of methanol and acetaldehyde.

In a sixth embodiment, the present invention is directed to a thermochemically formed ethanol composition comprising at least 92 wt. % ethanol, e.g., from 93 to 96 wt. % ethanol, less than 1 wt. % acetic acid, e.g., from 0.0001 to 0.01 wt. % acetic acid, and from 20 to 94 wppm isopropanol, e.g., from 20 to 80 wppm isopropanol, wherein the ethanol composition is free of methanol and acetaldehyde.

In a seventh embodiment, the present invention is directed to a thermochemically formed ethanol composition comprising at least 92 wt. % ethanol, e.g., from 93 to 96 wt. % ethanol, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

In an eighth embodiment, the present invention is directed to a thermochemically formed ethanol composition comprising at least 92 wt. % ethanol, e.g., from 93 to 96 wt. % ethanol, less than 1 wt. % acetic acid, e.g., from 0.0001 to 0.01 wt. % acetic acid, from 3 to 8 wt. % water, and from 20 to 94 wppm isopropanol, e.g., from 20 to 80 wppm isopropanol, wherein the ethanol composition is free of methanol and acetaldehyde.

In a ninth embodiment, the present invention is directed to a thermochemically formed ethanol composition comprising at least 92 wt. % ethanol, e.g., from 93 to 96 wt. % ethanol, from 3 to 8 wt. % water, less than 0.005 wt. % acetone, e.g., from 0.001 to 0.005 wt. % acetone, and from 20 to 94 wppm isopropanol, e.g., from 20 to 80 wppm isopropanol, wherein the ethanol composition is free of methanol and acetaldehyde.

In a tenth embodiment, the present invention is directed to a thermochemically formed ethanol composition comprising at least 92 wt. % ethanol, e.g., from 93 to 96 wt. % ethanol, from 3 to 8 wt. % water, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

In an eleventh embodiment, the present invention is directed to a thermochemically formed ethanol composition comprising at least 92 wt. % ethanol, e.g., from 93 to 96 wt. % ethanol, less than 0.005 wt. % acetone, e.g., from 0.001 to 0.005 wt. % acetone, less than 1 wt. % acetic acid, e.g., from 0.0001 to 0.01 wt. % acetic acid, and from 20 to 94 wppm isopropanol, e.g., from 20 to 80 wppm isopropanol, wherein the ethanol composition is free of methanol and acetaldehyde.

In a twelfth embodiment, the present invention is directed to a thermochemically formed ethanol composition comprising at least 92 wt. % ethanol, e.g., from 93 to 96 wt. % ethanol, less than 0.005 wt. % acetone, e.g., from 0.001 to 0.005 wt. % acetone, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

In a thirteenth embodiment, the present invention is directed to a thermochemically formed ethanol composition comprising at least 92 wt. % ethanol, e.g., from 93 to 96 wt. % ethanol, less than 1 wt. % acetic acid, e.g., from 0.0001 to 0.01 wt. % acetic acid, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

In a fourteenth embodiment, the present invention is directed to a thermochemically formed ethanol composition comprising at least 92 wt. % ethanol, e.g., from 93 to 96 wt. % ethanol, from 3 to 8 wt. % water, less than 1 wt. % acetic acid, e.g., from 0.0001 to 0.01 wt. % acetic acid, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

In a fifteenth embodiment, the present invention is directed to a thermochemically formed ethanol composition comprising at least 92 wt. % ethanol, e.g., from 93 to 96 wt. % ethanol, from 3 to 8 wt. % water, less than 0.005 wt. % acetone, e.g., from 0.001 to 0.005 wt. % acetone, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

In a sixteenth embodiment, the present invention is directed to a thermochemically formed ethanol composition comprising at least 92 wt. % ethanol, e.g., from 93 to 96 wt. % ethanol, less than 0.005 wt. % acetone, e.g., from 0.001 to 0.005 wt. % acetone, less than 1 wt. % acetic acid, e.g., from 0.0001 to 0.01 wt. % acetic acid, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

In an eighteenth embodiment, the present invention is directed to a thermochemically formed ethanol composition comprising at least 92 wt. % ethanol, e.g., from 93 to 96 wt. % ethanol, from 3 to 8 wt. % water, less than 0.005 wt. % acetone, e.g., from 0.001 to 0.005 wt. % acetone, less than 1 wt. % acetic acid, e.g., from 0.0001 to 0.01 wt. % acetic acid, less than 2 wt. % ethyl acetate, e.g., from 0.001 to 0.5 wt. % ethyl acetate, and from 20 to 94 wppm isopropanol, e.g., from 20 to 80 wppm isopropanol, wherein the ethanol composition is free of methanol and acetaldehyde.

BRIEF DESCRIPTION OF DRAWINGS

The invention is described in detail below with reference to the appended drawings, wherein like numerals designate similar parts.

DETAILED DESCRIPTION OF THE INVENTION

The present invention relates to processes for recovering an ethanol composition produced by a thermochemical process. The thermochemical process may include a hydrogenation process that reduces carbonyl-containing compounds to a mixture of alcohols. The mixture of alcohols for the purposes of the present invention comprises ethanol and at least one secondary alcohol. This mixture is referred to herein as the ethanol composition. Preferably, the hydrogenation process involves the hydrogenation of an alkanoic acid, e.g., acetic acid, and/or an ester thereof, e.g., ethyl acetate, in the presence of a catalyst. The ethanol composition may be purified to remove water, gases, and carbonyl impurities such as ethyl acetate, acetic acid, acetaldehyde, and diethyl acetal. The thermochemical process advantageously controls the amount of secondary alcohols, and in particular isopropanol in the ethanol composition. Advantageously, separation train for secondary alcohol is not needed to reduce the concentration of isopropanol. In one embodiment, it is surprisingly and unexpected that the isopropanol concentration may be control through the reactor temperature and thus reduce the amount of isopropanol in the ethanol composition without requiring separation to remove isopropanol. Coproducing a minor amount of isopropanol with ethanol allows for the introduction of minor amounts of alcohols that may adjust the alcohol strength of the ethanol composition. In addition, isopropanol does not adversely impact the use of ethanol in many different fields.

The inventive ethanol composition, in one embodiment, comprises a major portion of ethanol and a minor portion of isopropanol. The amount of water in the ethanol composition may be determined based on the end use of ethanol. For industrial ethanol application, the ethanol composition is primarily ethanol and contains from 92 wt. % to 96 wt. % ethanol, e.g., from 93 wt. % to 96 wt. %, or from 95 wt. % to 96 wt. %. Higher amounts of ethanol, for example anhydrous ethanol, may be possible by further removing the water as described herein. For high purity and fuel ethanol applications, the ethanol composition contains from 96 wt. % to 99.9 wt. % ethanol, e.g., from 98 wt. % to 99.9 wt. %, or from 99.5 wt. % to 99.9 wt. %. In either application, the isopropanol may be present in amounts ranging from 20 wppm to 94 wppm, e.g., from 20 wppm to 80 wppm, or from 20 wppm to 60 wppm. In one embodiment, isopropanol is the only secondary alcohol in the ethanol composition. The ethanol composition is preferably free of methanol and acetaldehyde.

In one embodiment, the ethanol composition further comprises water, for example, in an amount less than 8 wt. % water, e.g., less than 5 wt. % or less than 2 wt. %. In another embodiment, the ethanol composition comprises from 3 to 8 wt. % water. As previously described, the ethanol may be further dried to produce anhydrous ethanol, which may contain less than 0.5 wt. % water, e.g. less than 0.2 wt. %.

The ethanol composition may comprise less than 0.005 wt. % acetone, e.g., less than 0.001 wt. % or less than 0.0005 wt. %. Without being bound by theory, it is believed that isopropanol is formed during the hydrogenation of acetic acid. For example, the isopropanol may be formed via the hydrogenation of acetone. The acetone may be generated via an acetic acid ketonization reaction. In some embodiments, the ethanol composition is free of acetone. Without being bound by theory, the low amount or absence of acetone indicates that all acetone initially present in the ethanol composition has been hydrogenated to isopropanol. In addition, it is been surprisingly found that lower temperatures help to suppress formation of isopropanol. This allows for the introduction of minor amounts of isopropanol into the ethanol composition.

The ethanol composition may further comprise minor amounts of other impurities, including ethyl acetate, acetic acid, butanol, isobutanol, isoamyl alcohol, and other $C_4$ to $C_{20}$ alcohols. In these embodiments, the ethanol composition may comprise less than 1 wt. % acetic acid, e.g., less than 0.1 wt. %, less than 0.01 wt. %, less than 0.005 wt. %, or the ethanol composition may be free of acetic acid. The ethanol composition may comprise less than 2 wt. % ethyl acetate, e.g., less than 1 wt. %, less than 0.1 wt. %, less than 0.01 wt. %, or the ethanol composition may be free of ethyl acetate. Additional impurities, including butanol, isobutanol, isoamyl alcohol and other $C_4$ to $C_{20}$ alcohols may be present, in total, at less than 0.5 wt. % of the ethanol composition, e.g., less than 0.1 wt. %, less than 0.01 wt. %, less than 0.001 wt. %, or the ethanol composition may be free of these impurities.

The ethanol composition may also comprise n-propanol. The n-propanol, if present in the ethanol composition, is believed to be formed from impurities in the acetic acid feed used to form the ethanol composition. Without being bound by theory, the thermochemical process of the present invention does control the formation of n-propanol to the same extent as isopropanol. Thus, higher amounts of n-propanol may indicate impurities in the feed stream to the reactor. The ethanol compositions of the present invention preferably comprise n-propanol in an amount less than 0.05 wt. % n-propanol, e.g., less than 0.01 wt. % or less than 0.005 wt. %. Optionally, ethanol compositions of the present invention may preferably have less n-propanol than isopropanol. In one embodiment, the weight ratio of isopropanol to n-propanol in the inventive ethanol composition may range from 1:1 to 1:25 or from 1:1 to 1:22, from 1:1 to 5:1, or from 1:1 to 2:1.

In one embodiment of the present invention, isopropanol preferably is not added to the finished ethanol composition after the separation and recovery of ethanol. The isopropanol formed during the hydrogenation of acetic acid may be carried with the ethanol through the separation process.

Benzene, dioxanes, and cyanides are known to present toxicity issues in ethanol compositions. Typically, cyanides result from fermentation methods that utilize cassava as a feed stock. The inventive ethanol compositions comprise low amounts or are free of these components. Preferably, the ethanol composition contains no detectable amount of benzene, dioxanes, and cyanides.

As described further herein, in one embodiment, the ethanol composition is prepared by hydrogenating an alkanoic acid and/or an ester thereof to form a crude ethanol product and recovering a final ethanol product. The final ethanol product comprises at least 92 wt. % ethanol, from 20 to 94 wppm isopropanol, and is free of methanol and acetaldehyde. The water may be removed as needed depending on the ethanol application. The alkanoic acid may be acetic acid. Surprisingly and unexpectedly, it has been discovered that the temperature of the reactor influences isopropanol production by suppressing formation at lower temperatures. In conventional processes when hydrogenating acetone higher temperatures are used to suppress formation of isopropanol. In the present invention, as temperature increases, isopropanol production increases when the reaction is the hydrogenation of acetic acid. The increase in temperature may vary depending on the activity of the catalyst. In one embodiment, to control the amount of isopropanol, the reactor is operated in a controlled temperature range from 250° C. to 285° C., e.g., from 250° C. to 275° C., from 250° C. to 270° C. or from 250° C. to 265° C.

The ability to control the amount of isopropanol allows the alcoholic strength of the ethanol composition to be controlled. For example, an increase of approximately 20 wppm isopropanol may cause a decrease of 0.02 vol. % in alcoholic strength of the ethanol composition. Depending on the intended end use of the ethanol composition, the alcoholic strength may need to fit certain parameters with little to no deviation.

The present invention further comprises process controls for adjusting isopropanol content in the final ethanol composition. During the hydrogenation process, the temperature of the reactor may be adjusted to increase or decrease isopropanol content. Exceedingly high isopropanol amounts in the ethanol composition, e.g. of greater than 100 wppm, may indicate that the reactor is operated at a temperature that is too high for the catalyst activity. Thus, in one embodiment, the present invention is directed to controlling isopropanol content in an ethanol production process. Thus, isopropanol may be reduced without having to have a separate purification train. In particular, the ethanol is produced by hydrogenating acetic acid and/or an ester thereof in a reactor in the presence of a catalyst to form a crude ethanol product. The crude ethanol product is separated in at least one distillation column, as described herein, to recover the ethanol composition. The isopropanol content of the ethanol composition, or any stream containing ethanol that exits the distillation column, may be measured and the reactor temperature may then be adjusted accordingly to provide an ethanol composition ethanol composition having at least 92 wt. % ethanol and from 20 to 94 wppm isopropanol. The ethanol composition may be free of methanol and acetaldehyde, and in some embodiment, free of acetone. The reactor temperature is preferably between 250° C. and 280° C.

On-line analyzers may determine the isopropanol content in real or near time. The on-line analyzers suitable for use in the present invention include gas chromatograph, high-performance liquid chromatograph (HPLC), mass spectrometric, and infrared or near-infrared spectrometry. Preferably, the isopropanol concentration may be measured using a gas chromatograph analyzer. The measurement may be made in real time or in near-real time to provide feedback to the reactor to control the isopropanol concentration within an acceptable limit. The analyzer may also be used to determine the presence of other impurities in the ethanol composition.

Without being bound by theory, it is believed that the crude ethanol product is not concentrated enough to detect isopropanol concentration or that isopropanol has not yet formed in the crude ethanol product. As explained above, isopropanol may be present as the result of acetone formation from an acetic acid ketonization reaction. This reaction may occur during the ethanol separation steps, and thus for an accurate measurement of isopropanol, the measurement is made outside of the reactor and during the distillation process.

In one embodiment, the adjusting of the reactor temperature may comprise reducing the reactor temperature by at least 2° C., e.g., at least 5° C. or at least 10° C. when the isopropanol content in the intermediate ethanol product is greater than 100 wppm. In another embodiment, the adjusting of the reactor temperature may comprise increasing the reactor temperature by at least 2° C., e.g., at least 5° C. or at least 10° C. when the isopropanol content in the intermediate ethanol product is less than 20 wppm. The hydrogenation process and subsequent separation of ethanol is described in detail herein.

Hydrogenation Process

Turning to the production of the crude ethanol composition, generally, the hydrogenation of alkanoic acid, e.g., acetic acid and/or an ester thereof forms ethanol and water.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. In one embodiment, the production of ethanol may be integrated with a methanol carbonylation processes.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol stream may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Black liquor, which is an aqueous solution of lignin residues, hemicellulose, and inorganic chemicals, may also be used as a biomass source. Biomass-derived syngas has a detectable $^{14}C$ isotope content as compared to fossil fuels such as coal or natural gas.

In another embodiment, the acetic acid used in the hydrogenation step may be formed from the fermentation of biomass. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference.

The acetic acid fed to the hydrogenation reactor may also comprise acetic anhydride, acetaldehyde, ethyl acetate, propionic acid, water, and mixtures thereof. Propionic acid is less preferred because it leads to formation of higher primary alcohols. In one embodiment, the feed stream may comprise from 70 to 95 wt. % acetic acid and from 5 to 30 wt. % ethyl acetate.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

In preferred embodiments, the catalyst is employed in a fixed bed reactor where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 250° C. to 280° C., e.g., from 250° C. to 275° C., from 250° C. to 270° C., or from 250° C. to 260° C. The hydrogenation reactor pressure may range from 10 kPa to 3000 kPa, e.g., from 50 kPa to 2300 kPa. In one embodiment, the hydrogenation reaction is carried out at a pressure that is less than the hydration reaction pressure. The reactants may be fed to the reactor at a gas hourly space velocity (GHSV) ranging from 50 hr$^{-1}$ to 50,000 hr$^{-1}$, e.g., from 1000 hr$^{-1}$ to 10,000 hr$^{-1}$, or from 1000 hr$^{-1}$ to 6500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 20:1 to 1:2, or from 18:1 to 2:1.

The hydrogenation of acetic acid to form ethanol is preferably conducted in the presence of a hydrogenation catalyst in the reactor. In one embodiment, the hydrogenation catalyst may be a bifunctional catalyst and may convert acetic acid and ethyl acetate. The catalysts preferably are not methanol synthesis catalysts and are substantially free of copper and/or zinc, including oxides thereof. Suitable hydrogenation catalysts include catalysts comprising a first metal, a second metal, and optionally a third metal and on a catalyst support. Preferred bimetallic combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, nickel/palladium, gold/palladium, ruthenium/rhenium, and ruthenium/iron. Additional metal combinations may include palladium/rhenium/tin, palladium/rhenium/cobalt, palladium/rhenium/nickel, platinum/tin/palladium, platinum/tin/cobalt, platinum/tin/chromium, and platinum/tin/nickel. Exemplary hydrogenation catalysts are further described in U.S. Pat. Nos. 7,608,744 and 7,863,489 and U.S. Pub. No. 2010/0197985, the entireties of which are incorporated herein by reference.

In one embodiment, the hydrogenation catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. The first metal may be selected from the group consisting of platinum, palladium, cobalt, nickel, and ruthenium. The first metal may be present in the catalyst in an amount from 0.1 to 10 wt. %, e.g., from 0.1 to 5 wt. %, or from 0.1 to 3 wt. %.

The hydrogenation catalyst may further comprise a second metal selected from the group consisting of copper, molybdenum, tin, chromium, iron, cobalt, vanadium, tungsten, palladium, platinum, lanthanum, cerium, manganese, ruthenium, rhenium, gold, and nickel. Preferably, the second metal is different than the first metal. The second metal preferably is present in an amount from 0.1 to 20 wt. %, e.g., from 0.1 to 10 wt. %, or from 0.1 to 5 wt. %.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 7.5 wt. %, e.g., from 0.1 to 5 wt. %, or from 0.1 to 4 wt. %.

In addition to one or more metals, in some embodiments of the present invention the catalysts further comprise a support or a modified support. As used herein, the term "modified support" refers to a support that includes a support material and a support modifier, which adjusts the acidity of the support material. Modified supports are further described in U.S. Pat. No. 8,309,772, the entire contents and disclosures of which are hereby incorporated by reference.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst.

Suitable support materials may include, for example, include silicaceous supports, such as silica, silica/alumina, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$).

In one embodiment, the catalyst comprises from 0.5 to 5 wt. % platinum and from 0.5 to 10 wt. % tin on a modified support. The modified support comprises a silica support modified with a support modifier, such as calcium metasilicate.

In another embodiment, the catalyst comprises from 0.5 to 50 wt. % platinum, from 0.5 to 25 wt. % tin and from 4.1 to 20 wt. % cobalt on a modified support. The modified support comprises a silica support modified with a support modifier. The support material may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %. The modified support also comprises from 0.1 to 15 wt. % tin, provided that the total tin amount in the catalyst is not greater than 25 wt. %.

In yet another embodiment, the catalyst comprises from 0.5 to 50 wt. % platinum, from 0.5 to 25 wt. % tin and from 4.1 to 20 wt. % cobalt on a modified support. The modified support comprises a silica support modified with a support modifier. The support material may comprise from 5 to 15 wt. % acidic support modifiers, such as $WO_3$, $V_2O_5$ and/or $MoO_3$.

In one embodiment, the catalyst comprises from 0.25 to 1.25 wt. % platinum, and from 1 to 5 wt. % tin on a modified support. The modified support comprises a silica or a silica-alumina support material. The cobalt is disposed on the support material along with a support modifier. The support material may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %.

In particular, the hydrogenation of acetic acid may achieve favorable conversion of acetic acid and favorable selectivity and productivity to ethanol in the reactor. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 60%, or at least 80%. In those embodiments, it is preferred to achieve very high conversions that approach near 100% conversion.

Selectivity is expressed as a mole percent based on converted acetic acid. It should be understood that each compound converted from acetic acid has an independent selectivity and that selectivity is independent from conversion. In one embodiment, catalyst selectivity to ethanol is at least 60%, e.g., at least 70%, or at least 80%. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. A productivity from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol stream produced by the reactor, before any subsequent processing, such as purification and separation, will typically comprise the exemplary compositional ranges provided in Table 1. The "others" identified in Table 1 may include, for example, esters, ethers, aldehydes, ketones, alkanes, and carbon dioxide.

TABLE 1

CRUDE ETHANOL STREAM COMPOSITIONS

| Component | Conc. (wt. %) | Conc. (wt. %) | Conc. (wt. %) | Conc. (wt. %) |
| --- | --- | --- | --- | --- |
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | 0.1 to 2 |
| Isopropanol | ND | ND | ND | ND |

For purposes of the present invention, others may include acetone, diethyl acetal, and n-propanol. As shown in Table 1, it is difficult to determine the presence of isopropanol and it may not be detected directly out of the reactor. Even though isopropanol is not detectable in the crude ethanol stream, the isopropanol may build up in the separation process. Due to the buildup of isopropanol in the separation process, a separate distillation may otherwise be needed to remove isopropanol. The present invention recognizes a problem of isopropanol that could build up uncontrollably in the ethanol process and provides a thermochemical solution to run the hydrogenation at lower temperatures.

In one embodiment, the crude ethanol stream may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %.

Ethanol Separation

Ethanol produced from hydrogenation may be recovered using several different techniques. Regardless of the separation technique the present invention does not need a separate distillation or purification to remove secondary alcohols. The separation zone of FIG. 1 uses four columns. The separation zone of FIG. 2 employs two columns with an intervening water separation. The separation zone of FIG. 3 uses three columns. In some embodiment, the intervening water separation shown in FIG. 2 may also be used in FIG. 3. Other separation systems may also be used with embodiments of the present invention.

Figure 1:
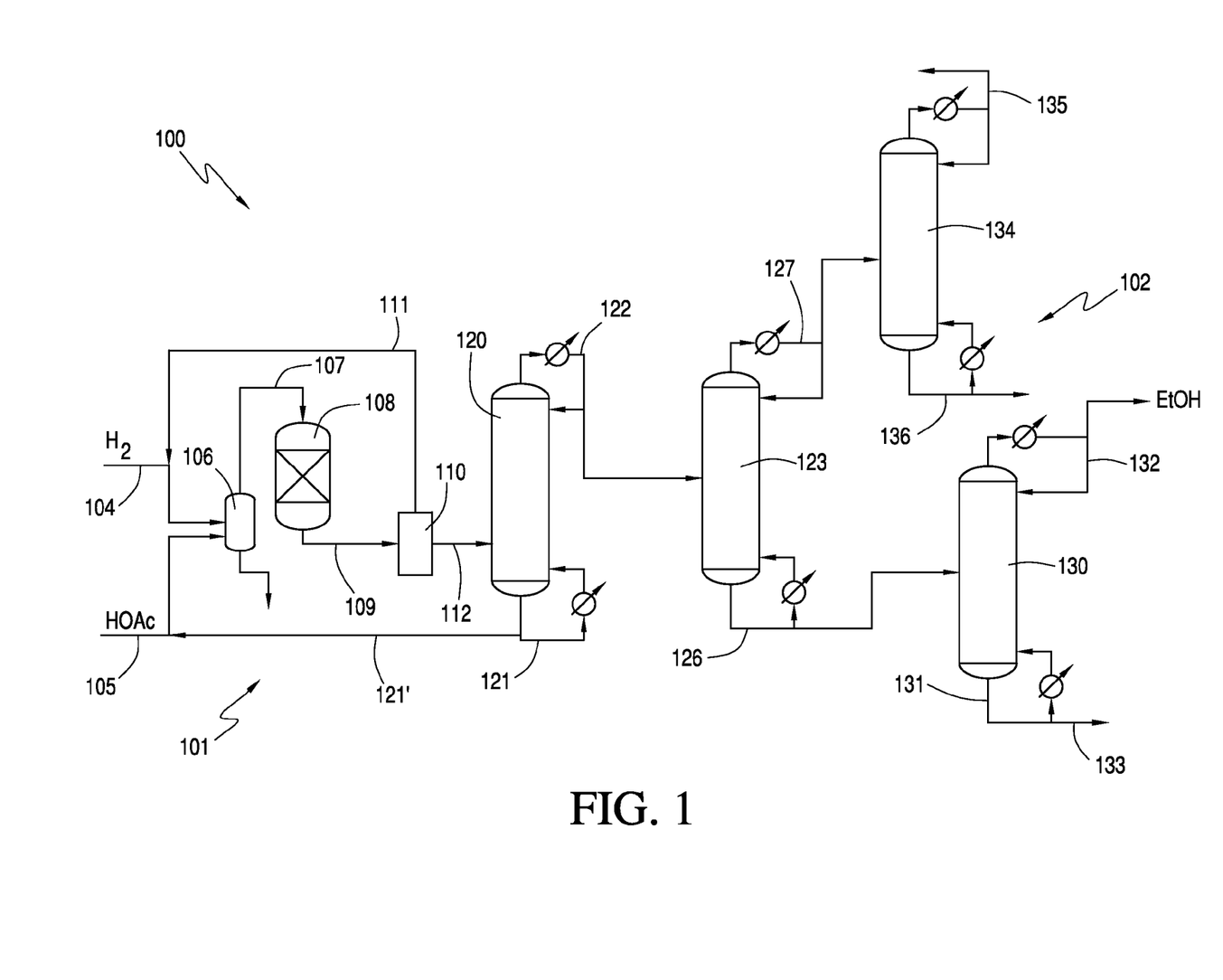
FIG. 1 is a schematic diagram of a hydrogenation system in accordance with one embodiment of the present invention.

Referring to FIG. 1, hydrogenation system 100 includes a hydrogenation reaction zone 101 and separation zone 102. Hydrogen and acetic acid via lines 104 and 105, respectively, are fed to a vaporizer 106 to create a vapor feed stream in line 107 that is directed to reactor 108. Hydrogen feed line 104 may be preheated to a temperature from 30° C. to 150° C. and a pressure from 1300 kPa to 3100 kPa. Acetic acid in line 105 may comprise fresh acetic acid, i.e., acetic acid that has not been previously exposed to a hydrogenation catalyst. Reactor 108 is a shell and tube reactor. Although one reactor is shown in FIGS. 2-4, multiple reactors and reactor beds may be used for in the hydrogenation reaction zone 101. In one embodiment, lines 104 and 105 may be combined and jointly fed to vaporizer 106. The temperature of the vapor feed stream in line 107 is preferably from 100° C. to 350° C.

As discussed above, reactor 108 contains the catalyst that is used in the hydrogenation of acetic acid. In one embodiment, the catalyst is preferably contained in a shell portion of reactor 108. During the hydrogenation process, a crude ethanol stream is withdrawn, preferably continuously, from reactor 108 via line 109.

Crude ethanol stream 109 may be condensed and fed to separator 110, which, in turn, provides a vapor stream 111 and a liquid stream 112. In some embodiments, separator 110 may be a flasher or a knockout pot. Separator 110 may operate at a temperature from 20° C. to 250° C., e.g., from 30° C. to 225° C., and a pressure from 50 kPa to 2000 kPa, e.g., from 75 kPa to 1500 kPa.

Vapor stream 111 exiting separator 110 may comprise hydrogen and hydrocarbons, and may be purged and/or returned to reaction zone 101 with hydrogen feed 104. In some embodiments, the returned vapor stream 111 may be compressed before being combined with hydrogen feed 104.

In FIG. 1, liquid stream 112 from separator 110 is withdrawn and pumped to the side of first column 120, also referred to as an "acid separation column." In one embodiment, the contents of liquid stream 112 are substantially similar to the crude ethanol stream obtained from the reactor, except that the composition has been depleted of hydrogen, carbon dioxide, methane and/or ethane, which are removed by separator 110. Accordingly, liquid stream 112 may also be referred to as a crude ethanol stream. Exemplary components of liquid stream 112 are provided in Table 2. It should be understood that liquid stream 112 may contain other components, not listed in Table 2.

TABLE 2

COLUMN FEED COMPOSITION
(Liquid Stream 112)

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 5 to 70 |
| Water | 5 to 30 | 5 to 28 | 10 to 26 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present specification may not be present and if present may be present in amounts greater than 0.0001 wt. %. Other alcohols may include isopropanol if detectable. As indicated above, it is difficult to detect isopropanol out of the reactor and after gases, such as hydrogen, are removed.

In the embodiment shown in FIG. 1, line 112 is introduced to the lower part of first column 120. In first column 120, unreacted acetic acid, a portion of the water, and other heavy components, if present, are removed from the composition in line 112 and are withdrawn, preferably continuously, as residue in line 121. Some or all of the residue may be returned and/or recycled back to reaction zone 101 via line 121'. Recycling the acetic acid in line 121' to the vaporizer 106 may reduce the amount of heavies that need to be purged from vaporizer 106. Reducing the amount of heavies to be purged may improve efficiencies of the process while reducing byproducts.

First column 120 also forms an overhead distillate, which is withdrawn in line 122, and which may be condensed and refluxed, for example, at a ratio from 10:1 to 1:10.

When column 120 is operated under standard atmospheric pressure, the temperature of the residue exiting in line 121 preferably is from 95° C. to 120° C., e.g., from 110° C. to 117° C. The temperature of the distillate exiting in line 122 preferably is from 70° C. to 110° C., e.g., from 75° C. to 95° C. First column 120 preferably operates at ambient pressure. In other embodiments, the pressure of first column 120 may range from 0.1 kPa to 510 kPa. Exemplary components of the distillate and residue compositions for first column 120 are provided in Table 3 below. For convenience, the distillate and residue of the first column may also be referred to as the "first distillate" or "first residue." The distillates or residues of the other columns may also be referred to with similar numeric modifiers (second, third, etc.) to distinguish them from one another, but such modifiers should not be construed as requiring any particular separation order.

TABLE 3

ACID COLUMN 120 (FIG. 1)

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

Isopropanol builds up in the distillate and concentrates with the ethanol being removed. The distillate in line 122 preferably comprises ethanol, ethyl acetate, and water, along with other impurities, which may be difficult to separate due to the formation of binary and tertiary azeotropes. To further separate distillate, line 122 is introduced to the second column 123, also referred to as the "light ends column," preferably in the middle part of column 123. Preferably second column 123 is an extractive distillation column, and an extraction agent is added thereto, via line 124. The extractive agent comprises water. The extractive agent may be obtained from hydration reaction zone 103 or third residue 131. In some embodiments, the extraction agent is fed from a source outside of process 100 via optional line 125 to second column 123.

In a tray column, the extractive agent in line 124 is continuously added near the top of second column 123 so that an appreciable amount of the extractive agent is present in the liquid phase on all of the trays below. The molar ratio of the water in the extraction agent to the ethanol in the feed to the second column may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

Other suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with a portion of third residue in line 131, and co-fed to the second column 123.

Second column 123 may be a tray column having from 5 to 70 trays or packed column. Although the temperature and pressure of second column 123 may vary, when at atmospheric pressure the temperature of the second residue exiting in line 126 is from 60° C. to 90° C., e.g., from 70° C. to 90° C. The temperature of the second distillate exiting in line 127 is from 50° C. to 90° C., e.g., from 60° C. to 80° C. In general, column 123 operates at atmospheric pressure, but also may operate over the range from 0.1 kPa to 510 kPa. Exemplary components for the distillate and residue compositions for second column 123 are provided in Table 4 below.

TABLE 4

SECOND COLUMN 123 (FIG. 1)

|  | Conc. (wt. %) | Conc. (wt. %) | Conc. (wt. %) |
|---|---|---|---|
| Distillate |  |  |  |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

Isopropanol is carried through the column with the majority of the ethanol in the residue. The weight ratio of ethanol in the second residue to second distillate preferably is at least 3:1, e.g., at least 6:1, or at least 15:1. All or a portion of the third residue is recycled to the second column. In one embodiment, all of the third residue may be recycled until system 100 reaches a steady state and then a portion of the third residue is recycled with the remaining portion being purged from system 100. The composition of the second residue will tend to have lower amounts of ethanol than when the third residue is not recycled. As the third residue is recycled, the composition of the second residue, as provided in Table 4, comprises less than 30 wt. % of ethanol. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

Figure 2:
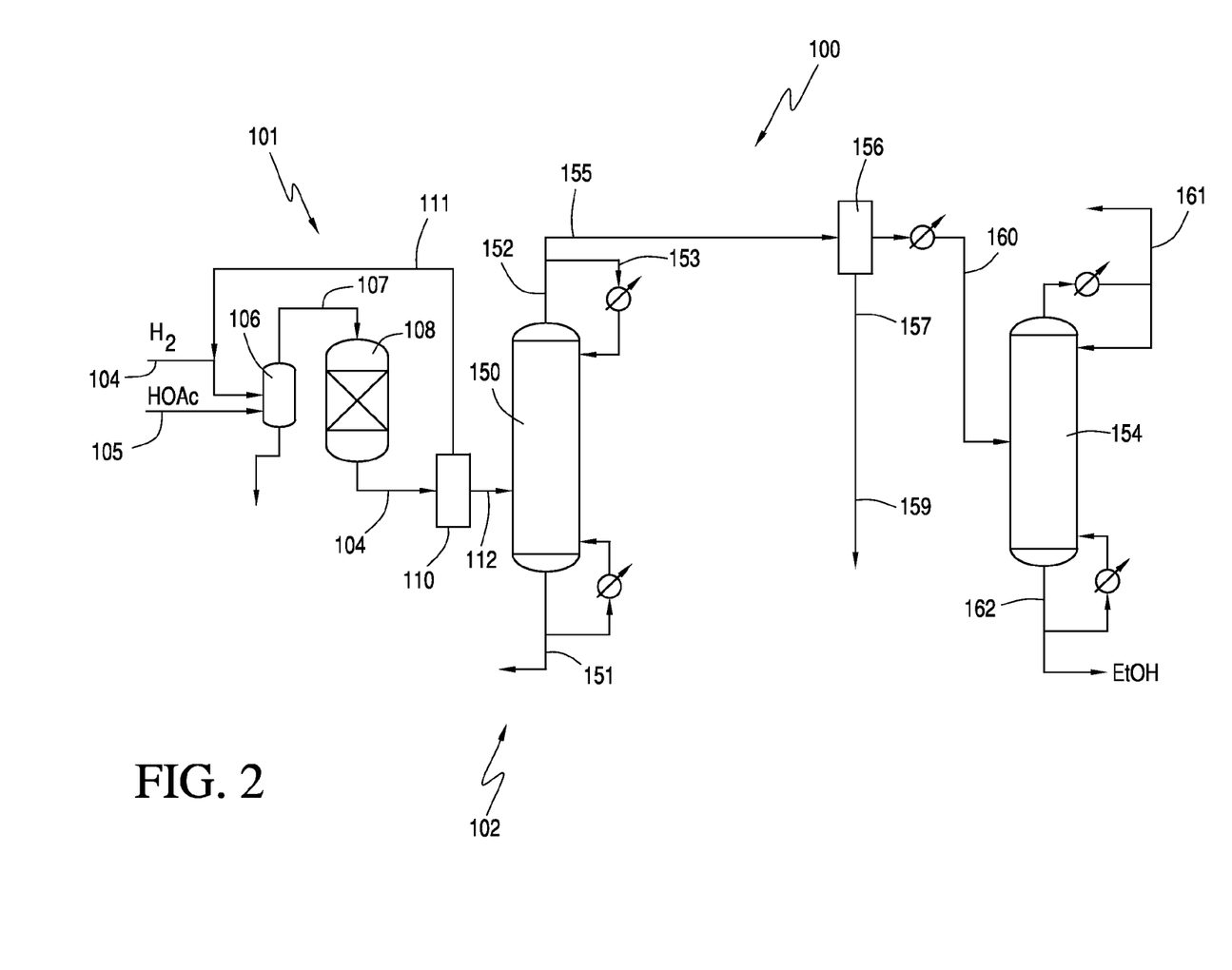
FIG. 2 is a schematic diagram of the reaction zone in accordance with another embodiment of the present invention.

As shown, the second residue from second column 123, which comprises ethanol and water, is fed via line 126 to third column 130, also referred to as the "product column." More preferably, the second residue in line 126 is introduced in the lower part of third column 130. Third column 130 recovers ethanol, which preferably is substantially pure with respect to organic impurities and other than the azeotropic water content, as the distillate in line 132. The distillate of third column 130 preferably is refluxed as shown in FIG. 2, for example, at a reflux ratio from 1:10 to 10:1.

Third column 130 is preferably a tray column as described above and operates at atmospheric pressure or optionally at pressures above or below atmospheric pressure. The temperature of the third distillate exiting in line 132 preferably is from 60° C. to 110° C., e.g., from 70° C. to 100° C. The temperature of the third residue in line 131 preferably is from 70° C. to 115° C., e.g., from 80° C. to 110° C. Exemplary components of the distillate and residue compositions for third column 130 are provided in Table 5 below.

TABLE 5

THIRD COLUMN 130 (FIG. 1)

|  | Conc. (wt. %) | Conc. (wt. %) | Conc. (wt. %) |
|---|---|---|---|
| Distillate |  |  |  |
| Ethanol | 90 to 96 | 92 to 96 | 93 to 96 |
| Water | 0.5 to 10 | 1 to 9 | 3 to 8 |
| Isopropanol | 20 wppm to 94 wppm | 20 wppm to 80 wppm | 20 wppm to 60 wppm |
| Acetic Acid | <1 | 0 to 0.1 | 0 to 0.05 |
| Ethyl Acetate | <2 | 0 to 0.05 | 0.001 to 0.025 |
| Acetaldehyde | <12 | 0.0001 to 0.1 | 0 to 0.05 |
| Diethyl Acetal | <2 | 0 to 0.5 | 0.005 to 0.025 |
| Residue |  |  |  |
| Water | 75 to 99.9 | 80 to 99.8 | 90 to 99.7 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

It should be understood that the isopropanol amounts may be higher when the reactor temperature is too high. This requires the process to detect higher isopropanol amounts and control the amount of isopropanol by adjusting the conditions of the reactor, namely the temperature.

Any of the compounds that are carried through the distillation process from the feed or crude reaction product generally remain in the third distillate in amounts of less 0.1 wt. %, based on the total weight of the third distillate composition. In one embodiment, one or more side streams may remove impurities from any of the columns in system 100. Preferably at least one side stream is used to remove impurities from the third column 130.

In one embodiment, a portion of third residue in line 131 may be purged via line 133. Once the process reaches steady state, a portion of water to be purged is substantially similar to the amount of water formed in the hydrogenation of acetic acid minus the water consumed during the hydration reaction.

The third residue in line 131, which comprises primarily water may be directed to second column 123 as an extraction agent as described above. In one embodiment, a first portion of the third residue in line 131 is recycled to second column 123 and a second portion is purged and removed from the system via line 133.

The third distillate in line 132 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 123, the second distillate preferably is refluxed as shown in FIG. 1, optionally at a reflux ratio of 1:10 to 10:1. The second distillate in line 127 may be purged or recycled to the reaction zone. In one embodiment, the second distillate in line 127 is further processed in fourth column 134, also referred to as the "acetaldehyde removal column." In fourth column 134 the second distillate is separated into a fourth distillate, which comprises acetaldehyde, in line 135 and a fourth residue, which comprises ethyl acetate, in line 136. The fourth distillate preferably is refluxed at a reflux ratio from 1:20 to 20:1, and a portion of the fourth distillate may be returned to reaction zone. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and used, with or without further purification, to make useful products including but not limited to n-butanol, 1,3-butanediol, and/or crotonaldehyde and derivatives.

The fourth residue of fourth column 134 may be purged. The fourth residue primarily comprises ethyl acetate and ethanol, which may be suitable for use as a solvent mixture or in the production of esters. In one preferred embodiment, the acetaldehyde is removed from the second distillate in fourth column 134 such that no detectable amount of acetaldehyde is present in the residue of column 134.

Fourth column 134 is preferably a tray column as described above and preferably operates above atmospheric pressure. In one embodiment, the pressure is from 120 kPa to 5,000 kPa, e.g., from 200 kPa to 4,500 kPa. The temperature of the fourth distillate exiting in line 135 preferably is from 60° C. to 110° C., e.g., from 70° C. to 100° C. The temperature of the residue in line 136 preferably is from 70° C. to 115° C., e.g., from 80° C. to 110° C. Exemplary components of the distillate and residue compositions for fourth column 134 are provided in Table 6 below.

TABLE 6

FOURTH COLUMN 134 (FIG. 1)

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

FIG. 2 illustrates another exemplary separation system. Hydrogenation reaction zone 101 of FIG. 2 is similar to that of FIG. 1. Reaction zone 101 produces liquid stream 112, e.g., crude ethanol stream. In one preferred embodiment, reaction zone 101 of FIG. 2 preferably operates at above 80% acetic acid conversion, e.g., above 90% conversion or above 99% conversion. Thus, the acetic acid concentration in the liquid stream 112 may be low.

Liquid stream 112 is introduced in the middle or lower portion of first column 150, also referred to as acid-water column. For purposes of convenience, the columns in each exemplary separation process, may be referred as the first, second, third, etc., columns, but it is understood that first column 150 in FIG. 2 operates differently than the first column 120 of FIG. 1. In FIG. 2, first column 150, water and unreacted acetic acid, along with any other heavy components, if present, are removed from liquid stream 112 and are withdrawn, preferably continuously, as a first residue in line 151. Preferably, a substantial portion of the water in the crude ethanol stream that is fed to first column 150 may be removed in the first residue, for example, up to about 75% or to about 90% of the water from the crude ethanol stream. First column 150 also forms a first distillate, which is withdrawn in line 152.

When column 150 is operated under about 170 kPa, the temperature of the residue exiting in line 151 preferably is from 90° C. to 130° C., e.g., from 95° C. to 120° C. The temperature of the distillate exiting in line 152 preferably is from 60° C. to 90° C., e.g., from 65° C. to 85° C. In some embodiments, the pressure of first column 150 may range from 0.1 kPa to 510 kPa.

The first distillate in line 152 comprises water, in addition to ethanol and other organics. In terms of ranges, the concentration of water in first distillate in line 152 preferably is from 4 wt. % to 38 wt. %. A portion of first distillate in line 153 may be condensed and refluxed, for example, at a ratio from 10:1 to 1:10. It is understood that reflux ratios may vary with the number of stages, feed locations, column efficiency and/or feed composition. The condensed portion of the first distillate may also be fed to second column 154.

The remaining portion of the first distillate in 155 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In an exemplary embodiment, water separator 156 is a pressure swing adsorption (PSA) unit. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 156 may remove at least 95% of the water from the portion of first distillate in line 155, and more preferably from 99% to 99.99% of the water from the first distillate, in a water stream 157. A portion of water stream 157 may be purged via line 159.

The remaining portion of first distillate exits the water separator 156 as ethanol mixture stream 160. Ethanol mixture stream 160 may have a low concentration of water of less than 10 wt. %, e.g., less than 6 wt. % or less than 2 wt. %. Exemplary components of ethanol mixture stream 160 and first residue in line 151 are provided in Table 7 below.

TABLE 7

FIRST COLUMN 150 WITH PSA (FIG. 2)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

Isopropanol builds up in the distillate and is carried through the water separator 156 into the ethanol mixture stream 160. Preferably, ethanol mixture stream 160 is not returned or refluxed to first column 150. The condensed portion of the first distillate in line 153 may be combined with ethanol mixture stream 160 to control the water concentration fed to the second column 154. For example, in some embodiments the first distillate may be split into equal portions, while in other embodiments, all of the first distillate may be condensed or all of the first distillate may be processed in the water separation unit. In FIG. 2, the condensed portion in line 153 and ethanol mixture stream 160 are co-fed to second column 154. In other embodiments, the condensed portion in line 153 and ethanol mixture stream 160 may be separately fed to second column 154. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 154 in FIG. 2, also referred to as the "light ends column," removes ethyl acetate and acetaldehyde from the first distillate in line 152 and/or ethanol mixture stream 160. Ethyl acetate and acetaldehyde are removed as a second distillate in line 161 and ethanol is removed as the second residue in line 162. Second column 154 may be a tray column, having from 5 to 70 trays, or packed column.

Second column 154 operates at a pressure ranging from 0.1 kPa to 510 kPa. Although the temperature of second column 154 may vary, when at about 20 kPa to 70 kPa, the temperature of the second residue exiting in line 162 preferably is from 30° C. to 75° C., e.g., from 35° C. to 70° C. The temperature of the second distillate exiting in line 161 preferably is from 20° C. to 55° C., e.g., from 25° C. to 50° C.

Optionally, when first distillate in line 153 and/or ethanol mixture stream 160 comprises less than 1 wt. % water, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators. Other extractive agents are described herein.

Exemplary components for the second distillate and second residue compositions for the second column 154 are provided in Table 8, below.

TABLE 8

| SECOND COLUMN 154 (FIG. 2) | | | |
|---|---|---|---|
| | Conc. (wt. %) | Conc. (wt. %) | Conc. (wt. %) |
| Second Distillate | | | |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue | | | |
| Ethanol | 80 to 99.5 | 85 to 97 | 60 to 95 |
| Water | <20 | 0.001 to 15 | 0.01 to 10 |

TABLE 8-continued

| SECOND COLUMN 154 (FIG. 2) | | | |
|---|---|---|---|
| | Conc. (wt. %) | Conc. (wt. %) | Conc. (wt. %) |
| Isopropanol | 20 wppm to 94 wppm | 20 wppm to 80 wppm | 20 wppm to 60 wppm |
| Ethyl Acetate | <1 | 0.001 to 2 | 0.001 to 0.5 |
| Acetic Acid | <0.5 | <0.01 | 0.001 to 0.01 |

Isopropanol is carried through the column with the majority of the ethanol in the residue. The second residue in FIG. 2 comprises one or more impurities selected from the group consisting of ethyl acetate, acetic acid, acetaldehyde, and diethyl acetal. The second residue may comprise at least 100 wppm of these impurities. In some embodiments, the second residue may contain substantially no ethyl acetate or acetaldehyde.

The second distillate in line 161, which comprises ethyl acetate and/or acetaldehyde, preferably is refluxed as shown in FIG. 2, for example, at a reflux ratio from 1:30 to 30:1. In one aspect, not shown, the second distillate in line 161 or a portion thereof may be returned to reactor 108. The ethyl acetate and/or acetaldehyde in the second distillate may be further reacted in reactor 108.

In one embodiment, the second distillate in line 161 and/or a refined second distillate, or a portion of either or both streams, may be further separated to produce an acetaldehyde-containing stream and an ethyl acetate-containing stream. This may allow a portion of either the resulting acetaldehyde-containing stream or ethyl acetate-containing stream to be recycled to reactor 108 while purging the other stream. The purge stream may be valuable as a source of either ethyl acetate and/or acetaldehyde.

Figure 3:
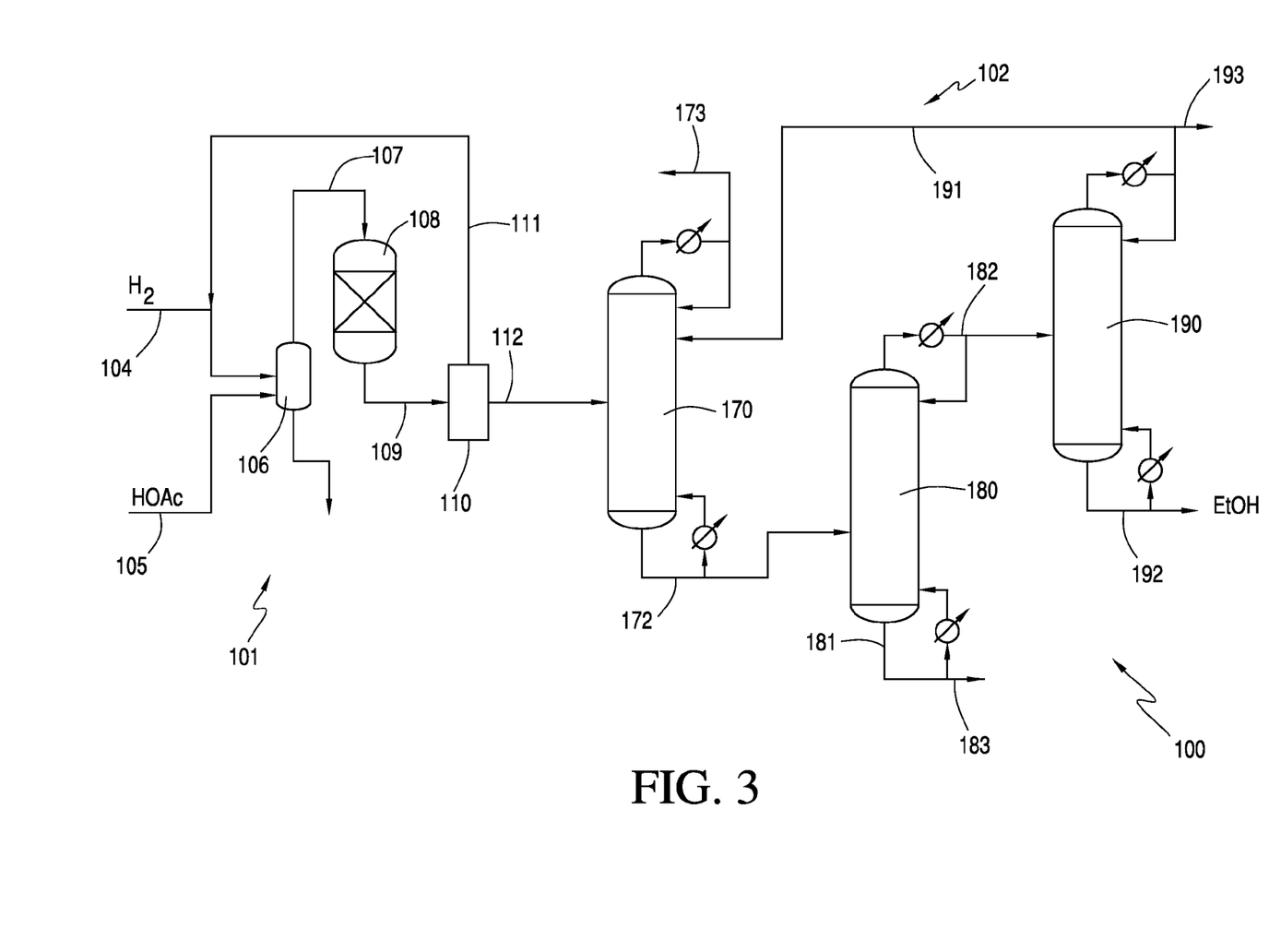
FIG. 3 is a schematic diagram of the reaction zone in accordance with another embodiment of the present invention.

The hydrogenation reaction zone 101 of FIG. 3 is similar to that of FIGS. 1 and 2 and produces liquid stream 112, e.g., crude ethanol stream, for further separation. In one preferred embodiment, the reaction zone 101 of FIG. 4 operates at above 80% acetic acid conversion, e.g., above 90% conversion or above 99% conversion. Thus, the acetic acid concentration in liquid stream 112 may be low.

Liquid stream 112 from separator 110 is withdrawn and directed as a feed composition to the side of first distillation column 170, also referred to as a "light ends column." Liquid stream 112 may be adjusted to have a temperature of up to 70° C. In the embodiment shown in FIG. 3, liquid stream 112 is introduced in the upper part of first column 170. An ethyl acetate recycle stream 191 may also be fed to first column 170 as shown in FIG. 3.

An optional extractive agent 171, which is the resulting stream from the hydration reaction zone 103 described below, may also be used and is preferably introduced above liquid stream 112. Extractive agent 171 may be adjusted to have a temperature of up to 70° C.

Extractive agent 171 preferably comprises water that has been retained within the system. As described herein, extractive agent 171 may be obtained from a portion of the second residue after hydration of the second residue. Extractive agent 171 may be a dilute acid stream comprising up to 20 wt. % acetic acid. Also because extractive agent 171 is from the hydration reaction, it may also comprise up to 20 wt. % ethanol. In one embodiment, the mass flow ratio of water in extractive agent 171 to the mass flow of the organic feed, which comprises liquid stream 112 and ethyl acetate recycle stream 191, may range from 0.05:1 to 2:1.

In one embodiment, first column 170 is a tray column having from 5 to 90 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 170 is operated under 50 kPa, the temperature of the residue exiting in line 172 preferably is from 20° C. to 100° C., e.g., from 30° C. to 90° C. The base of column 170 may be maintained at a relatively low temperature by withdrawing a residue stream comprising ethanol, ethyl acetate, water, and acetic acid, thereby providing an energy efficiency advantage. The temperature of the distillate exiting in line 173 from column 170 preferably at 50 kPa is from 10° C. to 80° C., e.g., from 20° C. to 70° C. The pressure of first column 170 may range from 0.1 kPa to 510 kPa.

In first column 170, a weight majority of the ethanol, water, acetic acid, are removed from the organic feed, including liquid stream 112 and ethyl acetate recycle stream 191, and are withdrawn, preferably continuously, as residue in line 172. This includes any water and ethanol added as an extractive agent 171. First column 170 also forms a distillate in line 173 that may be condensed and refluxed, for example, at a ratio from 30:1 to 1:30. Optionally, higher mass flow ratios of water, as an optional extractant, to organic feed may allow first column 170 to operate with a reduced reflux ratio. First distillate in line 173 preferably comprises a weight majority of the acetaldehyde and ethyl acetate from liquid stream 112, as well as from ethyl acetate recycle stream 191.

Exemplary components of the distillate and residue compositions for first column 170 are provided in Table 9 below.

TABLE 9

LIGHTS END COLUMN (FIG. 3)

| | Conc. (wt. %) | Conc. (wt. %) | Conc. (wt. %) |
|---|---|---|---|
| Distillate | | | |
| Ethyl Acetate | 10 to 85 | 15 to 80 | 20 to 75 |
| Acetaldehyde | 0.1 to 70 | 0.2 to 65 | 0.5 to 65 |
| Acetal | <3 | 0.01 to 2 | 0.05 to 1.5 |
| Acetone | <0.05 | 0.001 to 0.03 | 0.01 to 0.025 |
| Ethanol | <25 | 0.001 to 20 | 0.01 to 15 |
| Water | 0.1 to 20 | 1 to 15 | 2 to 10 |
| Acetic Acid | <2 | <0.1 | <0.05 |
| Residue | | | |
| Acetic Acid | 0.1 to 50 | 0.5 to 40 | 1 to 30 |
| Water | 20 to 85 | 25 to 80 | 30 to 75 |
| Ethanol | 10 to 75 | 15 to 70 | 20 to 65 |
| Ethyl Acetate | 0.005 to 30 | 0.03 to 25 | 0.08 to 1 |

Isopropanol is carried through the column with the majority of the ethanol in the residue. The weight ratio of water in the residue in line 172 to water in the distillate in line 173 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 108. In one embodiment, when the conversion in the hydrogenation reactor is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The first distillate in line 173 preferably is substantially free of acetic acid, e.g., comprising less than 1000 wppm acetic acid. The distillate may be purged from the system or recycled in whole or part to reactor 108.

To recover ethanol, first residue in line 172 may be further separated depending on the concentration of acetic acid and/or ethyl acetate. In most embodiments of the present invention, residue in line 172 is further separated in a second column 180, also referred to as an "acid column." Second column 180 yields a second residue in line 181 comprising acetic acid and water, and a second distillate in line 182 comprising ethanol and ethyl acetate. In one embodiment, a weight majority of the water and/or acetic acid fed to second column 180 is removed in the second residue in line 181, e.g., at least 60% of the water and/or acetic acid is removed in the second residue in line 181 or more preferably at least 80% of the water and/or acetic acid. Second column 180 also forms a second distillate in line 182 which may be condensed and refluxed, for example, at a ratio from 12:1 to 1:12.

Optionally, first residue in line 172 may be preheated prior to being introduced into second column 180. The first residue in line 172 may be heat integrated with either the residue or vapor overhead of the second column 180.

Second column 180 operates in a manner to concentrate the ethanol from first residue so that a majority of the ethanol is carried overhead. Thus, the residue of second column 180 may have a low ethanol concentration as shown in Table 10 below. Lower ethanol concentrations may be achieved without significant increases in reboiler duty or column size. Thus, in some embodiments it is efficient to reduce the ethanol concentration in the residue to less than 50 wppm.

In FIG. 3, the first residue in line 172 is introduced to second column 180 preferably in the top part of column 180. Acid column 180 may be a tray column having from 10 to 110 theoretical trays or packed column. Although the temperature and pressure of second column 180 may vary, when at atmospheric pressure the temperature of the second residue in line 181 preferably is from 95° C. to 160° C., e.g., from 100° C. to 150° C. or from 110° C. to 145° C. The temperature of the second distillate exiting in line 182 from second column 180 preferably is from 50° C. to 120° C., e.g., from 75° C. to 118° C. or from 80° C. to 115° C.

The pressure of second column 180 may range from 0.1 kPa to 510 kPa, e.g., from 1 kPa to 475 kPa or from 1 kPa to 375 kPa. In one embodiment, second column 180 operates above atmospheric pressure, e.g., above 170 kPa or above 375 kPa. Second column 180 may be constructed of a material such as 316L SS, Allot 2205 or Hastelloy C, depending on the operating pressure.

Exemplary components for the distillate and residue compositions for second column 180 are provided in Table 10 below. For example, in optional embodiments, when ethyl acetate is in the feed to reactor 108, second residue in line 181 exemplified in Table 10 may also comprise high boiling point components.

TABLE 10

ACID COLUMN (FIG. 3)

| | Conc. (wt. %) | Conc. (wt. %) | Conc. (wt. %) |
|---|---|---|---|
| Second Distillate | | | |
| Ethanol | 80 to 96 | 85 to 92 | 87 to 90 |
| Ethyl Acetate | <30 | 0.001 to 15 | 0.005 to 4 |
| Acetaldehyde | <20 | 0.001 to 15 | 0.005 to 4 |
| Water | <20 | 0.001 to 10 | 0.01 to 8 |
| Acetal | <2 | 0.001 to 1 | 0.005 to 0.5 |
| Second Residue | | | |
| Acetic Acid | 0.1 to 55 | 0.2 to 40 | 0.5 to 35 |
| Water | 45 to 99.9 | 55 to 99.8 | 65 to 99.5 |

TABLE 10-continued

| ACID COLUMN (FIG. 3) | | | |
|---|---|---|---|
| | Conc. (wt. %) | Conc. (wt. %) | Conc. (wt. %) |
| Ethyl Acetate | <0.1 | 0.0001 to 0.05 | 0.0001 to 0.01 |
| Ethanol | <5 | 0.002 to 1 | 0.005 to 0.5 |

The weight ratio of ethanol in second distillate in line 182 to ethanol in the second residue in line 181 preferably is at least 35:1. Preferably, second distillate in line 182 is substantially free of acetic acid and may contain, if any, trace amounts of acetic acid.

In one embodiment, ethyl acetate fed to second column 180 may concentrate in the second distillate in line 182. Thus, preferably no ethyl acetate is withdrawn in the second residue in line 181.

As discussed above, according to the present invention, unreacted acetic acid may be concentrated in the second residue in line 181. The second residue in line 181 may comprise from 85% to 99.99% of the unreacted acetic acid from the crude ethanol stream 109. In one embodiment, substantially all of the unreacted acetic acid is recovered in the second residue in line 181. By removing substantially all of the unreacted acetic acid from crude ethanol stream 109, the process, in some aspects, advantageously does not require further separation of acetic acid from the ethanol. In some embodiments, the dilute acid stream comprises from 0.1 to 55 wt. % acetic acid and from 45 to 99 wt. % water.

The second residue in line 181, which comprises primarily water, preferably is returned via line 171 to first column 170 as an extraction agent as described above. In one embodiment, a portion of second residue is purged and removed from the system via line 183. In one embodiment, once the process reaches steady state, the second portion of water to be purged is substantially similar to the amount water formed in the hydrogenation of acetic acid minus the water consumed during the hydration reaction. In some embodiments, a portion of alcohol recovery stream 145 may be used to hydrolyze any other stream, such as one or more streams comprising ethyl acetate or diethyl acetal.

In one embodiment, as shown in FIG. 3, due to the presence of ethyl acetate in second distillate in line 182, an additional third column 190 may be used. A third column 190, referred to as a "product" column, is used for removing ethyl acetate from second distillate in line 182 and producing an ethanol product in the third residue in line 192. Product column 190 may be a tray column having from 5 to 90 theoretical trays or packed column.

The feed location of second distillate in line 182 may vary and it is preferred to feed second distillate in line 182 to the upper portion of third column 190. Second distillate in line 182 may be fed to third column 190 at a temperature of up to 70° C.

Ethyl acetate may be concentrated in the third distillate in line 191. Due to the relatively lower amounts of ethyl acetate fed to third column 190, third distillate in line 191 also comprises substantial amounts of ethanol. To recover the ethanol, third distillate in line 191 may be fed to first column as an ethyl acetate recycle stream 191. Depending on the ethyl acetate concentration of ethyl acetate recycle stream 191 this stream may be introduced above or near the feed point of the liquid stream 112. Depending on the targeted ethyl acetate concentration in the distillate of first column 170 the feed point of ethyl acetate recycle stream 191 will vary. Liquid stream 112 and ethyl acetate recycle stream 191 collectively comprise the organic feed to first column 170. In one embodiment, organic feed comprises from 1 to 25% of ethyl acetate recycle stream 191. This amount may vary depending on the production of reactor 108 and amount of ethyl acetate to be recycled.

Because ethyl acetate recycle stream 191 increases the demands on the first and second columns, it is preferred that the ethanol concentration in third distillate in line 191 be from 70 to 90 wt. %, e.g., from 72 to 88 wt. %, or from 75 to 85 wt. %. In other embodiments, a portion of third distillate in line 191 may be purged from the system in line 193 as additional products, such as an ethyl acetate solvent. In addition, ethanol may be recovered from a portion of the third distillate in line 191 using an extractant, such as benzene, propylene glycol, and cyclohexane, so that the raffinate comprises less ethanol to recycle.

In an optional embodiment, the third residue may be further processed to recover ethanol with a desired amount of water, for example, using a further distillation column, adsorption unit, membrane or combination thereof, may be used to further remove water from third residue in line 192 as necessary.

Third column 190 is preferably a tray column as described above and preferably operates at atmospheric pressure. The temperature of the third residue in line 192 exiting from third column 190 preferably is from 65° C. to 110° C., e.g., from 70° C. to 100° C. The temperature of the third distillate in line 191 exiting from third column 190 preferably is from 30° C. to 70° C., e.g., from 40° C. to 65° C. The pressure of third column 190 may range from 0.1 kPa to 510 kPa. Exemplary components for ethanol mixture stream and residue compositions for third column 190 are provided in Table 11 below.

TABLE 11

| PRODUCT COLUMN (FIG. 3) | | | |
|---|---|---|---|
| | Conc. (wt. %) | Conc. (wt. %) | Conc. (wt. %) |
| Third Distillate | | | |
| Ethanol | 70 to 99 | 72 to 95 | 75 to 90 |
| Ethyl Acetate | 1 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue | | | |
| Ethanol | 80 to 99.5 | 85 to 97 | 90 to 95 |
| Isopropanol | 20 wppm to 94 wppm | 20 wppm to 80 wppm | 20 wppm to 60 wppm |
| Water | <3 | 0.001 to 2 | 0.01 to 1 |
| Ethyl Acetate | <1.5 | 0.0001 to 1 | 0.001 to 0.5 |
| Acetic Acid | <0.5 | <0.01 | 0.0001 to 0.01 |

In another embodiment, water may be removed prior to recovering the ethanol product as described above in FIG. 2 with the water separator 156. Second column 180 forms an overhead, which may comprise 85 to 92 wt. % ethanol, e.g., 87 to 90 wt. % ethanol, with the remaining balance being water and ethyl acetate. In one embodiment, the overhead may comprise less than 15 wt. % water, e.g., less than 10 wt. % water or less than 8 wt. % water. Overhead vapor from second column 180 may be fed to a water separator (not shown), as described above. Water separator may be an adsorption unit, membrane, molecular sieves, light ends column distillation, or a combination thereof. In one embodiment, at least 50% of overhead vapor is fed to water separator.

In another embodiment, the water separator may also be combined with a second hydration reactor as described above in FIG. 2.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The finished ethanol composition produced by the embodiments of the present invention may be used in a variety of applications including applications as fuels, solvents, chemical feedstocks, pharmaceutical products, cleansers, sanitizers, hydrogen transport or consumption. The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in US Pub. Nos. 2010/0030001 and 2010/0030002, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, non-limiting examples are provided below. The following examples describe various embodiments of the inventive ethanol composition.

EXAMPLES

Example 1

Several ethanol compositions were prepared using the hydrogenation process described above as well as the separation process. Crude ethanol products comprising ethanol, acetic acid, water and ethyl acetate were produced by reacting a vaporized feed comprising acetic acid with hydrogen in the presence of a catalyst. The temperature was varied from 245° C. to 298° C. and isopropanol content as a function of temperature was measured. The crude ethanol products were purified using a separation scheme having distillation columns as shown in FIG. 1.

Table 13 shows isopropanol compositional data for these ethanol compositions.

TABLE 13

| ISOPROPANOL CONTENT | |
|---|---|
| Temperature (° C.) | Isopropanol (wppm) |
| 248 | 12 |
| 254 | 20 |
| 260 | 40 |
| 265 | 60 |
| 270 | 76 |
| 276 | 100 |
| 282 | 116 |
| 287 | 136 |
| 295 | 162 |

Example 2

Several ethanol compositions comprising approximately 93.5 wt. % ethanol and approximately 6.5 wt. % water were tested for alcoholic strength. The compositions comprised from 0 to 1200 wppm isopropanol. Table 14 shows alcoholic strength as compared to isopropanol content in the ethanol compositions.

TABLE 14

| ALCOHOLIC STRENGTH | |
|---|---|
| Isopropanol (wppm) | Alcoholic Strength (vol. %) |
| 0 | 95.805 |
| 30 | 95.775 |
| 110 | 95.755 |
| 500 | 95.725 |
| 1200 | 95.725 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for controlling isopropanol content in an ethanol production process comprising:
   hydrogenating acetic acid and/or an ester thereof in a reactor in the presence of a catalyst to form a crude ethanol product;
   separating the crude ethanol product in at least one distillation column to recover an intermediate ethanol product;

measuring the content of isopropanol in the intermediate ethanol product, adjusting the temperature of the reactor, and recovering a finished ethanol product comprising at least 92 wt. % ethanol and from 20 to 94 wppm isopropanol, and wherein the finished ethanol product is free of methanol and acetaldehyde.

2. The process of claim 1, wherein the temperature in the reactor is between 250° C. and 280° C.

3. The process of claim 1, wherein the adjusting the temperature of the reactor comprises reducing the temperature of the reactor by at least 2° C. when the isopropanol content in the intermediate ethanol product is greater than 100 wppm.

4. The process of claim 1, wherein the adjusting the temperature of the reactor comprises increasing the temperature of the reactor by at least 2° C. when the isopropanol content in the intermediate ethanol product is less than 20 wppm.

5. The process of claim 1, wherein the finished ethanol product is free of acetone.

6. The process of claim 1, wherein the crude ethanol product is free of isopropanol.

7. The process of claim 1, wherein the finished ethanol product comprises from 20 to 80 wppm isopropanol.

8. The process of claim 1, wherein the finished ethanol product comprises from 3 to 8 wt. % water.

9. The process of claim 1, wherein the finished ethanol product comprises less than 0.005 wt. % acetone.

10. The process of claim 1, wherein the finished ethanol product comprises less than 1 wt. % acetic acid.

11. The process of claim 1, wherein the finished ethanol product comprises less than 2 wt. % ethyl acetate.

12. The process of claim 1, wherein the finished ethanol product comprises less than 0.5 wt. % butanol, isobutanol, isoamyl alcohol and $C_4$-$C_{20}$ alcohols.

13. The process of claim 1, wherein the hydrogenating is performed at a temperature from 250° C. to 275° C.

14. The process of claim 1, wherein the hydrogenating is in the presence of a catalyst on a support, wherein the catalyst comprises at least one active metal selected from the group consisting of cobalt, nickel, rhodium, palladium, osmium, iridium, platinum, titanium, zinc, chromium, rhenium, molybdenum, ruthenium, tin, vanadium, lanthanum, cerium, manganese, gold, and combinations thereof.

15. The process of claim 14, wherein the support comprises a support modifier selected from the group consisting of $TiO_2$, $ZrO_2$, $Ta_2O_5$, $Al_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$.

16. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

17. The process of claim 1, wherein the finished ethanol product comprises from 93 to 96 wt. % ethanol.

18. A process for controlling isopropanol content in an ethanol production process comprising:

hydrogenating acetic acid and/or an ester thereof in a reactor in the presence of a catalyst to form a crude ethanol product comprising ethanol, water, ethyl acetate and/or acetic acid, acetaldehyde, and isopropanol;

separating the crude ethanol product in at least one distillation column to recover a residue comprising ethanol and isopropanol;

measuring the content of isopropanol in the residue; and adjusting the temperature of the reactor in response to the measured isopropanol content to produce a finished ethanol product comprising at least 92 wt. % ethanol and from 20 to 94 wppm isopropanol in the third residue.

19. The process of claim 18, wherein the finished ethanol product is free of methanol and acetaldehyde.

20. The process of claim 18, wherein the temperature in the reactor is between 250° C. and 280° C.

* * * * *